US008865947B2

(12) United States Patent
Moloy et al.

(10) Patent No.: US 8,865,947 B2
(45) Date of Patent: Oct. 21, 2014

(54) PROCESS FOR PRODUCING FLUORINATED ALCOHOLS

(71) Applicant: E I du Pont de Nemours and Company, Wilmington, DE (US)

(72) Inventors: Kenneth Gene Moloy, Hockessin, DE (US); Sheng Peng, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/706,785

(22) Filed: Dec. 6, 2012

(65) Prior Publication Data

US 2014/0163262 A1      Jun. 12, 2014

(51) Int. Cl.
*C07C 29/132*  (2006.01)
*C07C 29/141*  (2006.01)
*C07C 29/60*   (2006.01)
*C07C 43/317*  (2006.01)
*C07C 45/51*   (2006.01)
*C07C 17/263*  (2006.01)

(52) U.S. Cl.
CPC ............. *C07C 29/141* (2013.01); *C07C 29/132* (2013.01); *C07C 43/317* (2013.01); *C07C 29/60* (2013.01); *C07C 45/513* (2013.01); *C07C 17/2637* (2013.01)
USPC ........... 568/842; 570/142; 568/495; 568/604; 568/677; 568/681; 568/683; 568/678

(58) Field of Classification Search
None
See application file for complete search history.

(56) References Cited

U.S. PATENT DOCUMENTS

| 3,979,469 | A | 9/1976 | Jager et al. |
| 5,481,028 | A | 1/1996 | Petrov et al. |
| 5,585,517 | A | 12/1996 | Deisenroth et al. |
| 6,506,947 | B1 | 1/2003 | Lina et al. |

FOREIGN PATENT DOCUMENTS

| CN | 102351651 | A | * | 2/2012 |
| JP | 04120041 | A | | 4/1992 |
| JP | 3350734 | B2 | | 11/2002 |

OTHER PUBLICATIONS

Huang, W-Y. et al. "Studies on sulfinatodehalogenation XV. Sodium dithionite-initiated addition of per- and polyfluoroalkyl halides to ethyl vinyl ether and chemical conversions of products" Chinese Journal of Chemistry 1990, 3, 281-288.*
Huang, W-Y. et al. "Studies on sulfinato-dehalogenation XII. Sodium dithionite-initiated addition of N, N-diethyliododifluoro acetamide to multiple bonds" Chinese Journal of Chemistry 1990, 1 68-74.*
Du, Y. et al. Patent No. CN102351651A; Feb. 15, 2012; English translation.*
"Raney Nickel Catalyst", pp. 1-3; Published on May 24, 2012.*
Legov et al, "Polyfluoroalkylation of vinyl ethers by heptafluoropropyl iodide in the presence of sodium alkoxides" (1994), (12), 2248-9. (Abstract).
Sasaoka et al "Alkoxyperfluoroalkylation of enol ethers catalyzed by iron complexes" (1991), (2), 86-7. (Abstract).
Zhu et al, Synthesis of 2-perfluoroalkyl-substituted acetals from the one-pot reaction of perfluoroalkyl iodides with vinyl ether and alcoholates (1996), 79(1), 77-79. (Abstract).
Huang et al, "Studies on sulfinato-dehalogenation. XII. Sodium dithionite-initiated addition of N,N-diethyliododifluoroacetamide to multiple bonds" Chinese Journal of Chemistry (1990), (1), 68-74. (Abstract).
Huang et al, "Studies on sulfinatodehalogenation. XV. Sodium dithionite-initiated addition of per- and polyfluoroalkyl halides to ethyl vinyl ether and chemical conversions of products" Chinese Journal of Chemistry (1990), (3), 281-8. (Abstract).
Huang et al, "Studies on sulfinatodehalogenation. XXI. A new and convenient synthesis of 2-(F-alkyl) aldehydes, alcohols, acids and ketones" Chinese Journal of Chemistry (1991), 9(2), 174-80. (Abstract).
Huang et al, "Studies on sulfinatodehalogenation. XXII. A new sulfinatodehalogenation reagent system: sodium bisulfite (NaHSO3)/potassium ferricyanide (K3[Fe(Cn)6])" Chinese Journal of Chemistry (1991), 9(4), 373-6. (Abstract).
Balague, et al, "Synthesis of fluorinated telomers, Part 1, Telomerization of vinylidene fluoride with perfluoroalkyl iodides", J. Fluorine Chem. (1995), 70(2), 215-23.
XP-002721286—TINAPP, Catalytic Reduction of the Carbonyl Group While Retaining Other Functions, pp. 207-212; Published Dec. 18, 1980.
International Search Report, PCT/US2013/073217, Filing date Dec. 5, 2013.

* cited by examiner

*Primary Examiner* — Fereydoun G Sajjadi
*Assistant Examiner* — Medhanit Bahta

(57) ABSTRACT

The present invention is directed to a process for preparation of fluorinated alcohols of Formula (I)

$$R_fCH_2CH_2OH \qquad (I)$$

by contacting a fluorinated iodide with an alkyl vinyl ether in the presence of an initiator and a base to generate an intermediate hemi-acetal or aldehyde or a mixture thereof, followed by hydrogenation of the hemi-acetal of Formula (II)

$$R_fCH_2CH(OC_xH_{2x+1})_m(OH)_p \qquad (II)$$

or aldehyde of Formula (III)

$$R_fCH_2CHO \qquad (III)$$

or a mixture thereof, to yield a compound of Formula (I).

20 Claims, No Drawings

PROCESS FOR PRODUCING FLUORINATED ALCOHOLS

FIELD OF INVENTION

The field of invention is related to the process selectively of producing fluorinated alcohols without the use of oleum or n-methyl formaldehyde.

BACKGROUND OF INVENTION

Fluorinated alcohols are generally prepared by reacting a fluorinated iodide and ethylene with oleum or n-methyl formaldehyde (NMF) followed by hydrolysis. Oleum is a strong oxidant and very corrosive. NMF requires high temperature heating for a prolonged time. One means to avoid use of such materials is the reaction of a fluorinated iodide with ethyl vinyl ether in aqueous acetonitrile in the presence of sodium dithionite and sodium bicarbonate to form acetaldehydes, followed by conversion of the acetaldehydes via a reduction in the presence of sodium borohydride to a mixture of alcohols, acids and esters as reported by Huang, Wei-Yuan et al., Chinese Journal of Chemistry (1990), (3), 281-288. This method then requires treatment of the mixture to obtain the alcohol.

It is desired to have a process for producing fluorinated alcohols without the use of harsh materials or conditions such as required when using oleum and NMF. It is also desired to have a process for producing fluorinated alcohols using simpler starting materials and milder reaction conditions. It is also desired to have a process that is more selective for alcohols, and does not yield predominately a mixture of alcohols, acids, and esters. The present invention provides such a process.

SUMMARY OF THE INVENTION

The present invention comprises a process for preparation of a compound of Formula (I)

$$R_fCH_2CH_2OH \qquad (I)$$

wherein
$R_f$ is linear or branched $C_nF_{2n+1}$ optionally interrupted intermittently by at least one oxygen, $CH_2$, or $CH_2CH_2$; and n is 1 to 10;
comprising
a) contacting a compound of formula $R_fI$, wherein $R_f$ is defined as above, with an alkyl vinyl ether containing 1 to 4 carbons in the alkyl, in the presence of an initiator and a base to generate an intermediate hemi-acetal of Formula (II) or aldehyde of Formula (III) or a mixture thereof $$R_fCH_2CH(OC_xH_{2x+1})_m(OH)_p \qquad (II)$$

$$R_fCH_2CHO \qquad (III)$$

wherein $R_f$ is defined as above, m is 0 to 1; and p is 1 to 2; provided that m+p is 2; and x is 1 to 4; and
b) hydrogenating the hemi-acetal of Formula (II) or aldehyde of Formula (III) or a mixture thereof to yield a compound of Formula (I).

DETAILED DESCRIPTION OF INVENTION

Trademarks are shown herein by capitalization.
The present invention comprises a process for preparation of a compound of Formula (I)

$$R_fCH_2CH_2OH \qquad (I)$$

wherein
$R_f$ is linear or branched $C_nF_{2n+1}$ optionally interrupted intermittently by at least one oxygen, $CH_2$, or $CH_2CH_2$; and n is 1 to 10;
comprising
a) contacting a compound of formula $R_fI$, wherein $R_f$ is defined as above, with an alkyl vinyl ether containing 1 to 4 carbons in the alkyl, in the presence of an initiator and a base to generate an intermediate hemi-acetal of Formula (II) or aldehyde of Formula (III) or a mixture thereof $$R_fCH_2CH(OC_xH_{2x+1})_m(OH)_p \qquad (II)$$

$$R_fCH_2CHO \qquad (III)$$

wherein $R_f$ is defined as above, and m is 0 to 1; p is 1 to 2 provided that m+p is 2; and x is 1 to 4; and
b) hydrogenating the hemi-acetal of Formula (II) or aldehyde of Formula (III) or a mixture thereof to yield a compound of Formula (I).

The moiety $R_f$ can be optionally interrupted with at least one oxygen, $CH_2$ or $CH_2CH_2$ group. Since subscript n is 1 to 10, $R_f$ can be interrupted with up to 9 such groups. Preferably $R_f$ is interrupted with 1 to 5 oxygen, $CH_2$ or $CH_2CH_2$ groups, and more preferably 1 to 3 such groups, and more preferably 1 to 2 such groups.

Preferred compounds of Formula (I) are those wherein for the group $R_f$, n is 1 to 6, more preferably 2 to 6, more preferably 3 to 6. Also preferred are those wherein $R_f$ is interrupted by 1, or 2 oxygen atoms.

Thus preferred embodiments of the present invention include the following:
A process for preparation of a compound of Formula (I)

$$R_fCH_2CH_2OH \qquad (I)$$

wherein
$R_f$ is linear or branched $C_nF_{2n+1}$ optionally interrupted intermittently by 1, 2, 3, 4, or 5 oxygen; or by 1, 2, 3, 4 or 5 $CH_2$, or by 1, 2, 3, 4 or 5 $CH_2CH_2$; and
n is 1 to 6; or n is 2 to 6; or n is 3 to 6; or n is 3, 4, 5 or 6;
comprising
a) contacting a compound of formula $R_fI$, wherein $R_f$ is defined as above, with an alkyl vinyl ether containing 1, 2, 3 or 4 carbons in the alkyl, in the presence of an initiator and a base to generate an intermediate hemi-acetal of Formula (II) or aldehyde of Formula (III) or a mixture thereof $$R_fCH_2CH(OC_xH_{2x+1})_m(OH)_p \qquad (II)$$

$$R_fCH_2CHO \qquad (III)$$

wherein $R_f$ is defined as above, m is 0 or 1; and p is 1 or 2; provided that m+p is 2; and x is 1, 2, 3, or 4; and
b) hydrogenating the hemi-acetal of Formula (II) or aldehyde of Formula (III) or a mixture thereof to yield a compound of Formula (I).

The process of the present invention begins by contacting a fluorinated iodide with an alkyl vinyl ether in the presence of an initiator and a base. The ratio of alkyl vinyl ether to $R_fI$ for the initial reaction is from about 1:1 to about 2:1. It is preferred to employ an excess of alkyl vinyl ether. The contacting of the iodide and alkyl vinyl ether is conducted at ambient temperature and pressure to yield an intermediate hemi-acetal or aldehyde, which is then hydrogenated to obtain an alcohol of Formula (I) as defined above.

Many of the simple starting iodides, such as $R_fI$, or $Rf(CH_2)_nI$ wherein n is 1 or more, suitable for use in the process of the present invention are commercially available. For example, such iodides can be obtained from Sigma Aldrich Inc., St Louis, Mo.

The starting fluorinated ether iodides, for example of formula $CF_3C_nF_{2n+1}$—O—$(CF_2)_m$I wherein m and n are each 1 or more, are made by the procedure described in U.S. Pat. No. 5,481,028, herein incorporated by reference, in particular by the procedure of Example 8, which discloses the preparation of these iodides from perfluoro-n-propyl vinyl ether. In this example 100 g (5 mole) of anhydrous HF, 10 g (0.147M) $BF_3$, and 45 g (0.3M) of hexafluoropropene were reacted in a 400 mL Hastelloy shaker tube previously cooled to −30° C. The reaction vessel was shaken 18 hours at 50° C. The gaseous products were then bled from the reaction vessel at 25 to 40° C. These gases were passed through a washing vessel containing 1000 mL of water, and the product was collected in a cooled trap (−78 degree C.). The product was isolated by distillation of crude product through a low temperature column. The same procedure can be employed using perfluoro-n-alkyl vinyl ether as a starting material to obtain other corresponding fluorinated ether iodides.

To obtain ether iodides also containing an ethylene group, for example of formula $R_f$—O—$CF_2CF_2$ $(CH_2CH_2)_q$I wherein q is 1 or more, the fluorinated iodide of formula $R_f$—O—$CF_2CF_2$I is reacted with an excess of ethylene at an elevated temperature and pressure. While the addition of ethylene can be carried out thermally, the use of a suitable catalyst is preferred. Preferably the catalyst is a peroxide catalyst such as benzoyl peroxide, isobutyryl peroxide, propionyl peroxide, or acetyl peroxide. More preferably the peroxide catalyst is benzoyl peroxide. The temperature of the reaction is not limited, but a temperature in the range of 110° C. to 130° C. is preferred. The reaction time varies with the catalyst and reaction conditions, but 24 hours is typically adequate. The product can be purified by any means that separates unreacted starting material from the final product, but distillation is preferred. Satisfactory yields up to 80% of theory have been obtained using about 2.7 mols of ethylene per mole of perfluoalkyl ether iodide, a temperature of 110° C. and autogenous pressure, a reaction time of 24 hours, and purifying the product by distillation.

The telomerization of vinylidene fluoride with linear or branched perfluoroalkyl iodides is known and produces iodides of the structure Rf $(CH_2CF_2)_q$I, wherein, q is 1 or more and $R_f$ is a $C_1$ to $C_{10}$ perfluoroalkyl group. For example, see Balague, et al, "Synthesis of fluorinated telomers, Part 1, Telomerization of vinylidene fluoride with perfluoroalkyl iodides", J. Fluorine Chem. (1995), 70(2), 215-23. The specific telomer iodides are isolated by fractional distillation. The telomer iodides are treated with ethylene by known procedures, for example as described in U.S. Pat. No. 3,979,469 to provide the telomer ethylene iodides of formula Rf $(CH_2CF_2)_q$ $(CH_2CH_2)_r$I wherein r is 1 to 3 or more.

In the present invention the iodide is contacted with an alkyl vinyl ether. Such ethers suitable for use in the present invention include those of linear or branched formula $CH_2$=$CHOC_xH_{2x+1}$, where x is 1to 4, Preferred alkyl vinyl ethers for use herein include methyl vinyl ether, ethyl vinyl ether, n-propyl vinyl ether, i-propyl vinyl ether, n-butyl vinyl ether, sec-butyl vinyl ether, tert-butyl vinyl ether, and isobutyl vinyl ether.

The present invention comprises contacting fluorinated iodides with an alkyl vinyl ether in the presence of an initiator and a base, Initiators useful in the present invention are acidic in nature. In particular oxides, sulfites, sulfinates, and nitrates are suitable initiators for use herein. Examples of such acidic initiators include, but are not limited to, benzoyl peroxide, sodium hydrosulfite ($Na_2S_2O_4$), thiourea dioxide (($NH_2$)$_2$ $CSO_2$), sodium metabisulfite ($Na_2S_2O_5$), sodium hydroxymethanesulfinate ($HOCH_2SO_2Na$), ammonium cerium (IV) nitrate (($NH_4$)$_2$Ce($NO_3$)$_6$) and potassium ferricyanide $K_3$[Fe(CN)$_6$].

The present invention comprises contacting fluorinated iodides with an alkyl ether with an initiator and a base. Suitable bases for use herein include oxides, hydroxides, carbonates, sulfites, and phosphates. In particular salts of alkali metals are preferred. Examples of such bases include, but not limited to, sodium bicarbonate ($NaHCO_3$), sodium bisulfite ($NaHSO_3$), calcium oxide (CaO), sodium carbonate ($Na_2CO_3$), sodium biphosphate ($Na_2HPO_4$), potassium hydroxide (KOH), sodium hydroxide (NaOH). The amount of base is used to balance the decomposition of the initiator and maintain the pH of the reaction mixture at from about 5 to about 10.

The process of the present invention proceeds with the initial formation of an intermediate hemi-acetal of Formula (II) $R_fCH_2CH(OC_xH_{2x+1})_m(OH)_p$ or an aldehylde of Formula (III) $R_fCH_2CHO$ or a mixture thereof as defined above. The formation of an intermediate acetal is avoided because it does not further react to form the desired alcohol product. The formation of the acetal is avoided by use of particular solvents. Suitable solvents include tetrahydrofuran, tetrahydropyran, glyme, and the like. The use of alcohols, nitriles, and acetonitriles are not suitable for use in the process of the present invention.

Hydrogenation

After the initial formation of an intermediate hemi-acetal of Formula (II) $R_fCH_2CH(OC_xH_{2x+1})_m(OH)_p$ or an aldehyde of Formula (III) $R_fCH_2CHO$ or mixture thereof as defined above, this intermediate is then hydrogenated. The hydrogenation of intermediate hemi-acetal of Formula (II) or aldehyde of Formula (III) or mixture thereof is achieved by contacting the intermediate with hydrogen gas in the presence of an aqueous acid and a catalyst. The hydrogenation of intermediate aldehyde of Formula (III) also occurs in the presence of a catalyst without the aqueous acid. The hydrogenation yields a product that is substantially the desired alcohol of Formula (I). Conversions of the intermediate to the alcohol of greater than 75% are typical, and conversions of 85%, 90%, or 95% are attainable. Conversions of 99% to 100% can be obtained. This is in contrast to prior art methods yielding mixtures of alcohols, acids, and esters, which then require isolation of the desired alcohol.

Catalysts useful in the hydrogenation of the intermediate hemi-acetals or aldehydes or mixture thereof to alcohols include neutral or acidic catalysts. Suitable catalysts include ruthenium, platinum, copper, or combinations thereof. These include, but are not limited to, ruthenium or platinum, each supported on carbon or aluminum oxide, and copper on various metal oxide supports such as zinc oxide or chromium oxide. Ruthenium and platinum loadings range are independently from 0.5% by weight to 10% by weight, preferably the loading range is about 5% by weight.

Aqueous acids useful in the hydrogenation step include sulfuric acid and phosphoric acid.

The hydrogenation is typically conducted at reduced pressure of atmospheric to about 600 psi (4.14 MPa) using hydrogen gas. Preferred is atmospheric to about 150 psi (1.03 MPa). Suitable temperatures for the hydrogenation is from about 25° C. to about 200° C. Preferred temperatures are from about 70° C. to about 150° C.

Solvents suitable for use in the hydrogenation step include ethers, such as tetrahydrofuran (THF) and glyme. The reaction is conducted with stirring to assure that the catalyst is fluidized during the reaction. The alcohol of Formula (I) is easily isolated using known processes such as distillation.

The process of the present invention provides several advantages over known prior art processes. The use of corrosive materials, such as oleum, is avoided. The use of high temperatures as required by n-methyl formaldehyde are also avoided. The desired alcohol is obtained at a high level of purity, thus avoiding product mixtures, for example of alcohols, acids, and esters, which require further separation steps. Simpler starting reactants are typically less costly, and milder reaction conditions are safer to use.

The process of the invention is useful in preparing fluorinated alcohols of Formula (I). The alcohols of Formula (I) are useful as starting monomers and intermediates to prepare a variety of compounds, polymers, and copolymers. Examples of such compounds, polymers, and copolymers include fluorinated surfactants and fluorinated treating agents for fibrous and hard surface substrates for imparting surface effects such as water repellency, oil repellency, soil resistance, or stain resistance. Such compounds, polymers, and copolymers can include acrylates, (meth)acrylates, urethanes, ureas, phosphates, ethers, vinyl ethers, esters, alkoxylates, and other derivatives.

MATERIALS AND METHODS

Materials
Fluorinated Iodides $C_6F_{13}I$ (Compound 1) was obtained, and is available from, from E. I. du Pont de Nemours and Company, Wilmington, Del., USA.

$C_3F_7OCF_2CF_2CH_2CH_2I$ (Compound 2) was prepared as follows.
Compound 2

$C_3F_7OCF_2CF_2I$ (100 g, 0.24 mol) and benzoyl peroxide (3 g) were charged to a pressure vessel under nitrogen. A series of three vacuum/nitrogen gas sequences was then executed at −50° C. and ethylene (18 g, 0.64 mol) was introduced. The vessel was heated for 24 hour at 110° C. The autoclave was cooled to 0° C. and opened after degassing. Then the product was collected in a bottle. The product was distilled giving 80 g of $C_3F_7OCF_2CF_2CH_2CH_2I$ in 80% yield. The boiling point was 56 to 60° C. at 25 mm Hg (3333 Pa).
Catalysts The following materials were obtained from Aldrich Chemical Company, Milwaukee, Wis.:
1) 5 wt % ruthenium on carbon,
2) Raney Nickel 2800, and
3) AMBERLYST 15.

The catalyst Ni-0104P, nickel supported on Kieselguhr, was supplied by Engelhard Corporation, Iselin, N.J.
Methods For hydrogenation reactions in the Examples, the following general procedure was employed. Hydrogenation was conducted in a custom reactor of Hastelloy C construction. A magnetic stir bar of length matching that of the diameter of the reactor bottom was used for mixing. This design ensured to the greatest degree possible that a dense heterogeneous catalyst would be fluidized during the experiment. After loading with reagents and sealing, the reactor was pressure tested with nitrogen and then pressurized with hydrogen. The reactor was brought to the target reaction temperature using an external heating block with integrated magnetic stirrer. Upon reaching the target temperature additional hydrogen was added as required for the experiment. Reaction progress was monitored by pressure drop using a pressure transducer with digital readout. Products were analyzed by gas chromatography (GC) using flame ionization (FID) and mass spectral (MS) detection. Product distributions are given as area percent from the FID and were not corrected for response factors.

EXAMPLES

Example 1

Sodium hydrosulfite (85% Tech grade, 24.4 g) was added to the mixture of Compound 1 (44.6 g), ethyl vinyl ether (9 g) and sodium bicarbonate (12 g) in the cosolvent of water (30 mL) and THF (50 mL) at 5° C. The reaction mixture was stirred for 5 hours, and the reaction was monitored via gas chromatography. 19F NMR showed greater than 98% hemiacetal formation ($R_fH<2$ mol %). The reaction mixture was filtered via a frit and the filtrate was subjected to vacuum transfer. The obtained hemi-acetal was passed for hydrogenation.

A pressure reactor was charged with 4.76 g of a mixture of $C_6F_{13}CH_2CHO$, $C_6F_{13}CH_2CH(OH)(OEt)$, EtOH, and THF, 0.5 g of 5% Ru/C, and 1.06 g of pH 2.2 water ($H_2SO_4$). The reactor was heated to 80° C. and pressurized to 140 psig (0.96 MPa) $H_2$. Gas uptake ceased after 3 hours and the reactor was cooled to room temperature and vented. Catalyst was removed by filtration and the filtrate analyzed by gas chromatography which showed 90% $C_6F_{13}CH_2CH_2OH$, 8% $C_5F_{11}CFHCH_2CH_2OH$, and 2% $C_6F_{13}CH_2CH_2OEt$.

Example 2

Sodium hydrosulfite (85% Tech grade, 24.4 g) was added to the mixture of Compound 1 (31.2 g), ethyl vinyl ether (9 g) and sodium bicarbonate (12 g) in a cosolvent of water (30 mL) and THF (50 mL) at 5° C. The reaction mixture was stirred for 5 hours, and the reaction was monitored via gas chromatography. 19F NMR showed greater than 98% hemiacetal formation ($R_fH<2$ mol %). The reaction mixture was filtered via a frit and the filtrate was subjected to vacuum transfer. The obtained mixture was hydrogenated in the presence of acid as follows.

A reactor was charged with 4.38 g of a mixture of $C_3F_7OCF_2CF_2CH_2CHO$, $C_3F_7OCF_2CF_2CH_2CH(OH)(OEt)$, EtOH, and THF, 0.408 g of 5% Ru/C, and 1.01 g of aqueous $H_2SO_4$ (pH 2.2). The reactor was pressurized with 400 psig (2.76 MPa) $H_2$ and stirred at room temperature for 1.5 h. The pressure dropped to 385 psig indicative of reaction. The reactor was heated to 80° C. to ensure complete reaction. After 2.5 h no further gas uptake was observed and the reaction was halted. The catalyst was removed by filtration and the filtrate was analyzed by gas chromatography, which showed nearly quantitative conversion to the alcohol $C_3F_7OCF_2CF_2CH_2CH_2OH$.

Example 3

Sodium hydrosulfite (85% Tech grade, 24.4 g) was added to the mixture of Compound 1 (31.2 g), ethyl vinyl ether (9 g) and sodium bicarbonate (12 g) in a cosolvent of water (30 mL) and THF (50 mL) at 5° C. The reaction mixture was stirred for 5 hours, and the reaction was monitored via gas chromatography. 19F NMR showed greater than 98% hemiacetal formation ($R_fH<2$ mol %). The reaction mixture was filtered via a frit and the filtrate was subjected to vacuum transfer. The obtained mixture was hydrogenated without added acid as follows.

A reactor was charged with 3.92 g of a mixture of $C_3F_7OCF_2CF_2CH_2CHO$, $C_3F_7OCF_2CF_2CH_2CH(OH)(OEt)$, EtOH, and THF, 0.336 g of 5% Ru/C, and 1.44 g of THF. The reactor was purged with hydrogen and then pressurized 142 psig (0.98 MPa). Stirring was commenced and the pressure drop was monitored. The pressure dropped to 120 psig over a 6 h period and then stopped. The reactor was vented and the catalyst removed by filtration. The filtrate was analyzed by gas chromatography, which showed nearly quantitative conversion to the alcohol $C_3F_7OCF_2CF_2CH_2CH_2OH$.

Example 4

The reaction of the fluorinated iodide and alkyl vinyl ether was conducted using a process as in Example 1. The hydrogenation was then conducted in the absence of acid. The hydrogenation reactor was charged with 0.5 g of Ru/C catalyst and 15.0 g of a mixture of $C_6F_{13}CH_2CHO$ and $C_6F_{13}CH_2CH(OH)(OEt)$ in THF. The reactor was brought to 80° C. and 2.1 MPa. After 3.5 h the reaction was halted and the reaction analyzed by GC and GCMS which showed quantitative conversion to a mixture of alcohol $C_6F_{13}CH_2CH_2OH$ (74%), ether $C_6F_{13}CH_2CH_2OEt$ (23%), and acetal $C_6F_{13}CH_2CH(OEt)_2$ (3%).

Example 5

The reaction of the fluorinated iodide and alkyl vinyl ether was conducted using a process as in Example 1. The hydrogenation was then conducted in the presence of an acid resin. The hydrogenation reactor was charged with 0.25 g 5% Ru/C, 0.25 g of AMBERLYST 15 acid resin, 5 mL of water, 5 mL of THF, and 1.0 g of a mixture of $C_6F_{13}CH_2CHO$ and $C_6F_{13}CH_2CH(OH)(OEt)$. The hydrogenation was conducted at 80° C. and 3.1 MPa for 3.5 h. GC analysis showed quantitative conversion to the desired alcohol $C_6F_{13}CH_2CH_2OH$. 1-butanol and 1,4-butanediol, resulting from hydrolysis and hydrogenation of the THF, were also observed.

Example 6

The reaction of the fluorinated iodide and alkyl vinyl ether was conducted using a process as in Example 1. The hydrogenation was then conducted in the presence of acid. The hydrogenation reactor was charged with 0.25 g of 5% Ru/C, 1.0 g of a mixture of $C_6F_{13}CH_2CHO$ and $C_6F_{13}CH_2CH(OH)(OEt)$, 5 mL of THF, and 5 mL of dilute $H_2SO_4$ (pH=2.2). The hydrogenation was conducted at 80° C. and 3.1 MPa for 3.5 h. GC analysis showed nearly quantitative formation of the desired alcohol $C_6F_{13}CH_2CH_2OH$ and only traces of other fluorinated products or products resulting from reaction of the THF solvent.

Example 7

The reaction of the fluorinated iodide and alkyl vinyl ether was conducted using a process as in Example 1. The reactor was charged with 5.0 grams of $C_6F_{13}CH_2CHO$ (containing <10% THF and EtOH) and 0.5 g of 5% Ru/C. The sample was hydrogenated at 50° C. and 0.97 MPa for 7 hours. GC analysis showed 97% conversion and 95% selectivity to $C_6F_{13}CH_2CH_2OH$.

Example 8

Example 7 was repeated at 80° C. and 0.97-0.90 MPa for 7 hours. GC analysis showed 98% conversion and 95% selectivity to $C_6F_{13}CH_2CH_2OH$.

Comparative Example A

The reaction of the fluorinated iodide and alkyl vinyl ether was conducted using a process as in Example 1. The reactor was charged with 0.5 g of 5% Ru/C and 6.2 grams of $C_6F_{13}CH_2CH(OEt)_2$ in 9.5 grams of THF. The sample was treated with hydrogen at 3.1 MPa and 80° C. for 3 hours. No pressure drop was noted. Analysis showed only unreacted $C_6F_{13}CH_2CH(OEt)_2$, demonstrating that the intermediate acetal does not hydrogenate.

Comparative Example B

The reaction of the fluorinated iodide and alkyl vinyl ether was conducted using a process as in Example 1. The reactor was charged with 0.5 g of 5% Ru/C, 5.0 g of aqueous $H_2SO_4$ (pH=2.2), and 15.0 grams of an ethanol mixture of a 9:1 mixture of $C_6F_{13}CH_2CH(OEt)_2$ and $C_6F_{13}CH_2CHO$ in ethanol. The sample was treated with hydrogen at 3.1 MPa and 80° C. for 3 hours. Analysis showed loss of the aldehyde, unreacted $C_6F_{13}CH_2CH(OEt)_2$, and a small amount of the alcohol $C_6F_{13}CH_2CH_2OH$. This example demonstrated that the acetal does not hydrogenate.

Comparative Example C

The reaction of the fluorinated iodide and alkyl vinyl ether was conducted using a process as in Example 1. A mixture of $C_6F_{13}CH_2CH(OH)(OEt)$ (10.4%) and $C_6F_{13}CH_2CH(OEt)_2$ (2.3%) in EtOH (12.0 grams) was treated at 80° C. and 3.1 MPa hydrogen in the presence of 0.5 g of 5% Ru/C and 5.0 g of aqueous $H_2SO_4$ (5.0 g). After 3 hours GC analysis showed only $C_6F_{13}CH_2CH(OEt)_2$ and no alcohol. This example demonstrated that the acetal does not hydrogenate.

Comparative Example D

The reaction of the fluorinated iodide and alkyl vinyl ether was conducted using a process as in Example 1. A solution of $C_6F_{13}CH_2CHO$ in acetonitrile (1.0 g) was charged to the reactor with 0.25 g of 5% Ru/C and 9 grams of heptane. The sample was treated with 3.1 MPa hydrogen at 85° C. for 1.5 h. GC showed conversion of the aldehyde to a mixture of the desired alcohol $C_6F_{13}CH_2CH_2OH$ containing $EtNH_2$, $Et_2NH$, $Et_3N$, and $C_6F_{13}CH_2CH_2NEt_2$. This example demonstrated that acetonitrile is not suitable as a solvent.

Comparative Example E

The reaction of the fluorinated iodide and alkyl vinyl ether was conducted using a process as in Example 1. A sample of 4.0 g of $C_6F_{13}CH_2CHO$ containing small amounts of EtOH, $C_6F_{13}CH_2CH(OH)(OEt)$, and $C_6F_{13}CH_2CH(OEt)_2$) in THF (5.0 g) was charged to the reactor with 0.25 g of Ni 0104P catalyst. The sample was treated with 4.1 MPa hydrogen at 80° C. for 1.5 h. GC showed conversion of the aldehyde to a mixture of $C_5F_{11}CF=CHCH_2OH$, $C_5H_{11}CFHCH_2OH$, $C_6F_{13}CH_2CH_2OEt$, and smaller amounts of other species. Only trace amounts of $C_6F_{13}CH_2CH_2OH$ were produced. This example demonstrated that nickel is not suitable as a catalyst.

Comparative Example F

The reaction of the fluorinated iodide and alkyl vinyl ether was conducted using a process as in Example 1. A sample of 4.0 g of $C_6F_{13}CH_2CHO$ containing small amounts of EtOH, $C_6F_{13}CH_2CH(OH)(OEt)$, and $C_6F_{13}CH_2CH(OEt)_2$) in THF (5.0 g) was charged to the reactor with 0.6 g of Raney Nickel catalyst 2800 slurry in water which had been previously washed with water. The sample was treated with 4.1 MPa hydrogen at room temperature for 18 hours. GC showed 100% aldehydes conversion to a mixture of $C_6F_{13}CH_2CH_2OH$ (34%), C6F13CH2CH2OEt (37%), and $C_5F_{11}CF=CHCH_2OH$ (28%). This example demonstrated that Raney Nickel is not optimal as a catalyst.

Example 9

Comparative Examples E and F were replicated with the exception that 0.25 g of 5% Ru/C was used instead of the nickel catalysts. After 2.5 hours at 3.4 MPa and 25° C. GC showed 79% conversion to a mixture of $C_6F_{13}CH_2CH_2OH$ (90%), $C_6F_{13}CH_2CH_2OEt$ (8%), and $C_6F_{13}CH_2CH(OEt)_2$ (2%).

Example 10

The reaction of the fluorinated iodide and alkyl vinyl ether was conducted using a process as in Example 1. The reactor was charged with 0.5 g of 5% Ru/C, 4.76 g of a mixture of $C_6F_{13}CH_2CHO$ (68%), $C_6F_{13}CH_2CH(OH)(OEt)$ (25%), and $C_5F_{11}CF=CHCHO$ (7%), and 1.06 g of aqueous $H_2SO_4$ (pH=2). The mixture was hydrogenated at 80° C. and 2.8 MPa for 2.5 hours. GC showed 100% conversion to $C_6F_{13}CH_2CH_2OH$ (94%), $C_5F_{11}CFHCH_2CH_2OH$ (4%), and $C_6F_{13}CH_2CH_2OEt$ (2%).

Example 11

The reaction of the fluorinated iodide and alkyl vinyl ether was conducted using a process as in Example 2. The reactor was charged with 4.38 g of the aldehyde (containing a small amount of ethanol), 0.41 g of 5% Ru/C, 1.26 g of THF, and 1.0 g of aqueous $H_2SO_4$ (pH 2.2). The mixture was hydrogenated at 80° C. and 3.1 MPa for 2.5 h. GC showed 100% conversion to 99% pure $C_3F_7OCF_2CF_2CH_2CH_2OH$.

Example 12

The reaction of the fluorinated iodide and alkyl vinyl ether was conducted using a process as in Example 2. The reactor was charged with 3.92 g of the aldehyde (containing a small amount of ethanol), 0.34 g of 5% Ru/C, and 1.44 g of THF. The sample was treated with 0.97-0.83 MPa hydrogen at 22° C. Gas uptake ceased after 7-8 hours. GC analysis showed 100% conversion to 98% pure $C_3F_7OCF_2CF_2CH_2CH_2OH$.

What is claimed is:

1. A process for preparation of a compound of Formula (I)

$$R_fCH_2CH_2OH \qquad (I)$$

wherein
$R_f$ is linear or branched $C_nF_{2n+1}$ optionally interrupted by at least one oxygen, $CH_2$, $CH_2CH_2$, or $CH_2CF_2$; and
n is 1 to 10;
comprising
a) contacting a compound of formula $R_fI$, wherein $R_f$ is defined as above, with an alkyl vinyl ether containing 1 to 4 carbons in the alkyl, in the presence of an initiator and a base to generate a mixture of intermediates comprising an hemi-acetal of Formula (II) and an aldehyde of Formula (III)

$$R_fCH_2CH(OC_xH_{2x+1})_m(OH)_p \qquad (II)$$

$$R_fCH_2CHO \qquad (III)$$

wherein $R_f$ is defined as above, m is 0 to 1; and p is 1 to 2; provided that m+p is 2; and x is 1 to 4; and b) hydrogenating, under acidic conditions, the mixture comprising the hemi-acetal of Formula (II) and aldehyde of Formula (III) to yield a compound of Formula (I).

2. The process of claim 1 wherein the ratio of alkyl vinyl ether to $R_fI$ is from about 1:1 to about 2:1.

3. The process of claim 1 wherein the alkyl vinyl ether is of the formula $CH_2=CHOC_xH_{2x+1}$ wherein x is 1 to 4.

4. The process of claim 1 wherein the alkyl vinyl ether is selected from the group consisting of methyl vinyl ether, ethyl vinyl ether, n-propyl vinyl ether, i-propyl vinyl ether, n-butyl vinyl ether, sec-butyl ether, tert-butyl vinyl ether, and isobutyl vinyl ether.

5. The process of claim 1 wherein the initiator is an oxide, sulfite, sulfinate or nitrate.

6. The process of claim 1 wherein the initiator is selected from the group consisting of benzoyl peroxide, sodium hydrosulfite, thiourea dioxide, sodium metabisulfite, sodium hydroxymethanesulfinate, ammonium cerium(IV) nitrate and potassium ferricyanide.

7. The process of claim 1 wherein the base is an oxide, hydroxide, carbonate, sulfite or phosphate.

8. The process of claim 7 wherein the base is selected from the group consisting of sodium bicarbonate, sodium bisulfite, calcium oxide, sodium carbonate, potassium carbonate, sodium pyrophosphate, potassium hydroxide, and sodium hydroxide.

9. The process of claim 1 wherein the contacting of $R_fI$ with an alkyl vinyl ether is conducted at ambient temperature.

10. The process of claim 1 wherein the contacting of $R_fI$ with an alkyl vinyl ether is in a solvent selected from the group consisting of tetrahydrofuran, tetrahydropyran, and glyme.

11. The process of claim 1 wherein the hydrogenating of the mixture of intermediates comprising the hemi-acetal of Formula (II) and aldehyde of Formula (III) is in the presence of 1) an aqueous acid and 2) a catalyst selected from the group consisting of ruthenium, platinum, copper, and combinations thereof.

12. The process of claim 1 wherein the hydrogenating of the mixture of intermediates comprising the hemi-acetal of Formula (II) and aldehyde of Formula (III) is in the presence of a catalyst selected from the group consisting of ruthenium, platinum, copper, and combinations thereof.

13. The process of claim 11 wherein the ruthenium or platinum catalyst is supported on carbon or aluminum oxide, and wherein the copper catalyst is supported on zinc oxide or chromium oxide.

14. The process of claim 12 wherein the ruthenium or platinum catalyst is supported on carbon or aluminum oxide, and wherein the copper catalyst is supported on zinc oxide or chromium oxide.

15. The process of claim 11 wherein the aqueous acid is selected from the group consisting of sulfuric acid and phosphoric acid.

16. The process of claim 11 conducted at a temperature ranging from about 25° C. to about 200° C., and a pressure at from about atmospheric to about 600 psi (4.14 MPa).

17. The process of claim 12 conducted at a temperature ranging from about 25° C. to about 200° C., and a pressure at from about atmospheric to about 600 psi (4.14 MPa).

18. The process of claim 1 wherein for $R_f$, n is 1 to 6.

19. The process of claim 1 wherein $R_f$ is interrupted by 1 or 2 oxygen atoms.

20. The process of claim 1 wherein the alcohol of Formula (I) is generated with an overall yield of the whole process of greater than 75%.

* * * * *